(12) United States Patent
Nagakura et al.

(10) Patent No.: US 8,795,632 B2
(45) Date of Patent: Aug. 5, 2014

(54) DISEASE ANIMAL MODEL FOR CHRONIC PAIN

(75) Inventors: Yukinori Nagakura, Tokyo (JP); Tomoya Oe, Tokyo (JP)

(73) Assignee: Astellas Pharma Inc., Chuo-Ku, Tokyo (JP)

( * ) Notice: Subject to any disclaimer, the term of this patent is extended or adjusted under 35 U.S.C. 154(b) by 68 days.

(21) Appl. No.: 13/001,743

(22) PCT Filed: Oct. 7, 2009

(86) PCT No.: PCT/JP2009/067460
§ 371 (c)(1),
(2), (4) Date: Dec. 28, 2010

(87) PCT Pub. No.: WO2010/070971
PCT Pub. Date: Jun. 24, 2010

(65) Prior Publication Data
US 2011/0110862 A1    May 12, 2011

(30) Foreign Application Priority Data
Dec. 16, 2008  (JP) ............... P2008-319048

(51) Int. Cl.
*A01K 67/00* (2006.01)
*A61K 49/00* (2006.01)
*A61P 43/00* (2006.01)

(52) U.S. Cl.
USPC .............................. 424/9.2; 800/9

(58) Field of Classification Search
None
See application file for complete search history.

(56) References Cited

U.S. PATENT DOCUMENTS 6,009,875 A  *  1/2000  Hubbard, Jr. ................ 128/898

OTHER PUBLICATIONS

Kulkarni et al (European Journal of Pharmacology. 1982; 83: 325-328).*
Nagakura et al. (Pain. 2009; 146(1-2): 26-33).*
Lee et al. (Neuropharmacology. 2006; 51: 557-565).*
Leith et al. (Psychopharmacology. 1980; 72: 9-15).*
Asanuma, Masato; Ogawa, Norio; Haba, Kumiko; Hirata, Hiroshi; and Mori, Akitane, "Effects of chronic catecholamine depletions on muscarinic M1-receptor and its mRNA in rat brain", Journal of the Neurological Sciences, vol. 110, 1992, pp. 205-214.
Wood, Patrick B.; Schweinhardt, Petra; Jaeger, Erik; Dagher, Alain; Hakyemez, Helene; Rabiner, Eugenii A.; Bushnell, M. Catherine; and Chizh, Boris A., "Fibromyalgia patients show an abnormal dopamine response to pain", European Journal of Neuroscience, vol. 25, 2007, pp. 3576-3582.
Nagakura, Yukinori; Oe, Tomoya; Aoki, Toshiaki; and Matsuoka, Nobuya, "Biogenic amine depletion causes chronic muscular pain and tactile allodynia accompanied by depression: A putative animal model of fibromyalgia", Pain, vol. 146, 2009, pp. 26-33.
Staud, Roland, and Rodriguez, Miguel E., "Mechanisms of Disease: pain in fibromyalgia syndrome", Nature Clinical Practice Rheumatology, vol. 2, 2006, pp. 90-98.
Cook, Dane B.; Lange, Gudrun; Ciccone, Donald S.; Liu, Wen-Ching; Steffender, Jason; and Natelson, Benjamin H., "Functional Imaging of Pain in Patients with Primary Fibromyalgia", Journal of Rheumatology, vol. 31, 2004, pp. 364-378.
Mountz, MD, PhD, James M.; Bradley, PhD, Laurence A.; and Alarcón, MD, MPH, Graciela S., "Abnormal Functional Activity of the Central Nervous System in Fibromyalgia Syndrome", The American Journal of the Medical Sciences, vol. 315, 1998, pp. 385-396.
Wood, Patrick B.; Holman, Andrew J.; and Jones Kim D., "Novel pharmacotherapy for fibromyalgia", Current Opinion in Investigational Drugs, vol. 16, 2007, pp. 829-841.
Harris, Richard E.; Sundgren, Pia C.; Pang, Yuxi; Hsu, Michael; Petrou, Myria; Kim, Seong-Ho; McLean, Samuel A.; Gracely, Richard H.; and Clauw, Daniel J., "Dynamic Levels of Glutamate Within the Insula Are Associated with Improvements in Multiple Pain Domains in Fibromyalgia", Arthritis & Rheumatism, vol. 58, Mar. 2008, pp. 903-907.
Ablin, Jacob; Neumann, Lily; and Buskila, Dan, "Pathogenesis of fibromyalgia—A review", Joint Bone Spine, vol. 75, 2008, pp. 273-279.
Mease, Philip J.; Russell, I. Jon; Arnold, Lesley M.; Florian, Hana; Young Jr., James P.; Martin, Susan A.; and Sharma, Uma, "A Randomized, Double-blind, Placebo-Controlled, Phase III Trial of Pregabalin in the Treatment of Patients with Fibromyalgia", The Journal of Rheumatology, vol. 35, 2008, pp. 502-514.
Russell, I. Jon; Mease, Philip J.; Smith, Timothy R.; Kajdasz, Daniel K.; Wohlreich, Madelaine M.; Detke, Michael J.; Walker, Daniel J.; Chappell, Amy S.; and Arnold, Lesley M., "Efficacy and safety of duloxetine for treatment of fibromyalgia in patients with or without major depressive disorder: Results from a 6-month, randomized, double-blind, placebo-controlled, fixed-dose trial", Pain, vol. 136, 2008, pp. 432-444.
Holman, Andrew J., and Myers, Robin R., "A Randomized, Double-Blind, Placebo-Controlled Trial of Pramipexole, A Dopamine Agonist, in Patients with Fibromyalgia Receiving Concomitant Medications", Arthritis & Rheumatism, vol. 52, No. 5, Aug. 2005, pp. 2495-2505.
Kehl, Lois J.; Trempe, Thomas M.; Hargreaves, Kenneth M., "A new animal model for assessing mechanisms and management of muscle hyperalgesia", Pain, vol. 85, 2000, pp. 333-343.
Sluka, PhD, K.A.; Kalra, A.; and Moore, MD, PhD, S.A., "Unilateral Intramuscular Injections of Acidic Saline Produce a Bilateral, Long-Lasting Hyperalgesia", Muscle & Nerve, vol. 24, 2001, pp. 37-46.
Suarez-Roca, Heberto; Quintero, Luis; Arcaya, Jose Luis; Maixner, William; and Rao, Srinivas G., "Stress-induced muscle and cutaneous hyperalgesia: Differential effect of milnacipran", Physiology & Behavior, vol. 88, 2006, pp. 82-87.

(Continued)

*Primary Examiner* — Scott Long
(74) *Attorney, Agent, or Firm* — Finnegan, Henderson, Farabow, Garrett & Dunner, L.L.P.

(57) ABSTRACT

A disease animal model, characterized in that a chronic pain is induced by applying a treatment for reducing the biogenic amine level to a mammal, and a method for screening for a therapeutic agent for a chronic pain, characterized in that a test substance is administered to said disease animal model.

7 Claims, 8 Drawing Sheets

(56) References Cited

OTHER PUBLICATIONS

Kulkarni, Shrinivas K., and Robert, Rejit K., "Reversal by Serotonergic Agents of Reserpine-Induced Hyperalgesia in Rats", European Journal of Pharmacology, vol. 83, 1982, pp. 325-328.

Yokoyama, Takeshi; Maeda, Yumi; Audette, Katherine M.; and Sluka, Kathleen A., "Pregabalin Reduces Muscle and Cutaneous Hyperalgesia in Two Models of Chronic Muscle Pain in Rats", The Journal of Pain, vol. 8, No. 5, May 2007, pp. 422-429.

Heslop, K. E., and Curzon, G., "Depletion and Repletion of Cortical Tissue and Dialysate 5-HT After Reserpine", Neuropharmacology, vol. 33, No. 3-4, 1994, pp. 567-573—XP-002638176.

Bars, Le Daniel; Gozariu, Manuela; and Cadden, Samuel W., "Animal Models of Nociception", Pharmacological Reviews, vol. 53, No. 4, 2001, pp. 597-652—XP-002338281.

Mogil, Jeffrey S., and Crager, Sara E., "What should we be measuring in behavioral studies of chronic pain in animals?", Pain, vol. 112, 2004, pp. 12-15—XP-004604750.

Casey, Kenneth L., and Dubner, Ronald, "Animal models of chronic pain: scientific and ethical issues", Pain, vol. 38, 1989, pp. 249-252—XP-024378960.

Manolescu M.D.; R., and Elian M.D., I., "Treatment of Residual Pain after Peripheral Surgical Revascularization by Intra Arterial Administration of Reserpine", Pain, vol. 18, 1984, p. S392—XP-024381190.

Lief, P. A.; Reisman, R.; Rocco, A.; McKay, W.; Kaul, A.; and Benfell, K., "I.V. Regional Guanethidine vs. Reserpine for Pain Relief in Reflex Sympathetic Dystrophy (RSD); A Controlled, Randomized, Double-Blind, Crossover Study", vol. 30, 1987, p. S205—XP-026744457.

Tsukamoto M.; OE, T.; and Nagakura Y., "Reserpine Causes Biphasic Nociceptive Sensitivity Alteration in Conjunction with Brain Biogenic Amine Tones in Rats", Neuroscience, vol. 169, No. 4, 2010, pp. 1860-1871—XP-027197744.

Letters to the Editor—"Comment on Biogenic amine depletion as a putative animal model of fibromyalgia", Pain, vol. 148, 2010, pp. 172-173.

Letters to the Editor—"Response to the "Letter to the Editor of Pain" by Dr. Munro", Pain, vol. 148, 2010, pp. 173-174.

Commentary—Is it possible to develop an animal model of fibromyalgia?, Pain, vol. 146, 2009, pp. 3-4—XP-002638178.

Huang, Qing-jun; Jiang, Hong; Hao, Xin-ling; and Minor, Thomas R., "Brain IL-1β was involved in reserpine-induced behavioral depression in rats", Acta Pharmacol Sinica, vol. 25, 2004, pp. 293-296.

English translation of Office Action for corresponding Japanese Patent Application No. 2010-542910, dated Jul. 12, 2011.

Supplemental European Search Report for EP Application No. 09833276, dated May 31, 2011.

\* cited by examiner

DISEASE ANIMAL MODEL FOR CHRONIC PAIN

TECHNICAL FIELD

The present invention relates to a disease animal model in which a chronic pain, particularly chronic muscle pain and/or chronic tactile allodynia, is induced by a treatment for decreasing the biogenic amine level, and a method for screening for a therapeutic agent for a chronic pain, particularly fibromyalgia, which uses said disease animal model.

BACKGROUND ART

The pain is defined as an unpleasant sense which is accompanied by existing tissue damage or is expressed from such an experience, or an experience of an emotional action (International Association for the Study of Pain, 1979), and is divided into an acute pain and a chronic pain.

In the acute pain, a nociceptive stimulus which violates a tissue of the biological body is input into a peripheral nociceptor, converted into an action potential and transferred as an impulse to the spinal cord, at which it is influenced by various inhibitory system such as descending system, and ascends the sensory transfer system and reaching the cerebral cortex, so that the acute pain is recognized. That is, the acute pain is a physiological pain caused by a nociceptive stimulus, and has a significance as a warning reaction in the biological body. The acute pain disappears by cancellation of the nociceptive stimulus or healing of the injury.

On the other hand, the chronic pain is a pain which is complained regardless of the healing of tissue injury or a pain which is complained regardless of the absence of evident tissue injury. That is, the chronic pain is "a pain which is complained regardless of exceeding the period generally necessary for healing of the disease, or a pain related to progressive non-cancerous diseases".

The chronic pain does not have a physiological significance as a biological body warning system unlike the case of acute pains and, what is more, it greatly spoils quality of life of patients. Thus, the chronic pain is an independent disease and requires a treatment, namely elimination of pain, but most cases of the chronic pain are intractable.

The fibromyalgia is a disease which has a systemic unbearable chronic pain as the core symptom accompanied by various comorbid symptoms such as sleeplessness, systemic fatigue feeling, depressive symptom and the like. Diagnostic standards of the American College of Rheumatology are the continuation of a pain over broad range of the body for 3 months or more and the presence of tenderness at 11 points or more among the 18 tender points on the whole body (ligaments, tendons, muscles and the like contacting with bones). It is sometimes accompanied by a pain caused by a tactile stimulus or cold stimulus which does not generally cause a pain, called tactile allodynia or cold allodynia. In addition, it is also frequently accompanied by a thermal hyperalgesia in which sensitivity for thermal stimulus is accelerated. Since prevalence rate of fibromyalgia is about 2% of the population, a considerably large number of patients are present. However, since a sufficiently effective therapeutic method is not present, concern has been strongly directed toward the development of a new therapeutic method having high efficacy.

Pathophysiological mechanism of fibromyalgia is not sufficiently revealed. Since the systemic unbearable chronic pain and various comorbid symptoms such as sleeplessness, systemic fatigue feeling, depressive symptom and the like, as the characteristics of fibromyalgia, cannot be fully described by a peripheral level abnormality, it is considered that an abnormality of pain-controlling mechanism of the central nervous system is participated in the pathophysiological mechanism of fibromyalgia (e.g., see Non-patent Reference 1). Actually, results of studies which used a functional magnetic resonance imaging (fMRI) and a single-photon emission tomography (SPET) show that there is an abnormality in the brain function of fibromyalgia patients (e.g., see Non-patent References 2 and 3).

Quantitative changes and functional abnormalities of various neurotransmitters, cytokines or hormones are suggested on fibromyalgia patients. Concentration of excitatory amino acid, substance P or nerve growth factor in the cerebrospinal fluid of fibromyalgia patients is higher in comparison with that of the non-patient groups. On the other hand, metabolite concentration of serotonin, dopamine or norepinephrine in the cerebrospinal fluid of fibromyalgia patients is lower in comparison with that of the non-patient groups (e.g., see Non-patent Reference 4). It has been reported that there is a correlation between the amount of excitatory amino acid as a brain excitatory transmitter in brain insula and the pain level of fibromyalgia patients (e.g., see Non-patent Reference 5).

In addition, it has been reported that there is an abnormality in the release mechanism of brain dopamine for a pain stimulus in fibromyalgia patients (e.g., see Non-patent Reference 4). Cytokines such as interleukin-1 and tumor necrosis factor (Tumor Necrosis Factor) have been detected from the skin tissue of fibromyalgia patients (e.g., see Non-patent Reference 6). In addition, it has been suggested that the secretion function of growth hormone or insulin-like growth factor (IGF) is reduced in fibromyalgia patients (e.g., see Non-patent Reference 4). Thus, a possibility has been suggested that many neurotransmitters, cytokines or hormones and the like are contributed to the pathophysiological mechanism of fibromyalgia, but it has not been revealed yet that which change is the causal pathogenesis and which one is the consequent phenomenon. That is, pathophysiological mechanism of fibromyalgia has not been revealed yet (e.g., see Non-patent Reference 6).

Recently, it has been reported that pregabalin (a nerve $Ca^{2+}$ channel ligand), duloxetine (a selective serotonin and norepinephrine reuptake inhibitor) or pramipexole (a dopamine receptor agonist) alleviates the pain symptom score of fibromyalgia patients statistically significantly in comparison with the placebo group (e.g., see Non-patent References 7 to 9).

However, effects of these drugs are limited, and there is no therapeutic method yet which is sufficiently effective on the pain-centered symptoms of fibromyalgia patients. Accordingly, there is a strong demand for the development of a further excellent therapeutic agent which has sufficient effects and shows fewer side effects.

In general, validity of a disease animal model is evaluated from the viewpoint of face validity (whether or not the model and human disease symptomatically resemble), construct validity (whether or not the model is based on the theoretical ground) and predictive validity (whether or not the effects of therapeutic agent in the model and clinical setting are correlated). As the disease animal model of the chronic pain which is accompanied by muscle pain, there have been reported a method in which carrageenan or acidic water is intramuscularly injected (e.g., see Non-patent References 10 and 11) and a method in which a repeated forced swimming load is applied (e.g., see Non-patent Reference 12). However, there has not been reported so far on an animal model which sufficiently reflects the pathophysiological mechanism of fibromyalgia from the viewpoint of face validity, construct validity and predictive validity.

Regarding the pain inducing action of reserpine, it has so far been reported that single intraperitoneal administration of reserpine causes hypersensitivity to thermal stimulation in rats. However, it has been reported that this hypersensitivity to thermal stimulation is a transient acute pain which disappears within 24 hours (e.g., see Non-patent Reference 13). Induction of the generation of a pain by reserpine over a long period of time of 1 day or more has not been reported yet.

Non-patent Reference 1: Nature Clinical Practice Rheumatology, 2006, vol. 2, p. 90-97
Non-patent Reference 2: Journal of Rheumatology, vol. 31, p. 364-378
Non-patent Reference 3: American journal of the Medical Science, 1998, vol. 315, p. 385-396
Non-patent Reference 4: Current Opinion in Investigational Drugs, 2007, vol. 16, p. 829-841
Non-patent Reference 5: Arthritis & Rheumatism, 2008, vol. 58, p. 903-907
Non-patent Reference 6: Joint Bone Spine, 2008, vol. 75, p. 273-279
Non-patent Reference 7: The Journal of Rheumatology, 2008, vol. 35, p. 502-514
Non-patent Reference 8: Pain, 2008, vol. 136, p. 432-444
Non-patent Reference 9: Arthritis & Rheumatism, 2005, vol. 52, p. 2495-2505
Non-patent Reference 10: Pain, 2000, vol. 35, p. 333-343
Non-patent Reference 11: Muscle & Nerve, 2000, vol. 24, p. 37-46
Non-patent Reference 12: Physiology & Behavior, 2006, vol. 88, p. 82-87
Non-patent Reference 13: European Journal of Pharmacology, 1982, vol. 83, p. 325-328

DISCLOSURE OF THE INVENTION

Problems that the Invention is to Solve

For the purpose of creating a therapeutic agent for fibromyalgia, a disease animal model is essential which reflects the pathophysiological mechanism of fibromyalgia from the viewpoint of face validity, construct validity and predictive validity and also can carry out screening of a test substance efficiently. However, a disease animal model which fully satisfies such conditions has not been reported.

Accordingly, the present inventors have carried out intensive studies with the aim of developing a disease animal model which persistently generates chronic pain symptoms of muscle pain and tactile allodynia and depressive symptoms, which are characteristic symptoms of fibromyalgia, and also has excellent predictability of clinical effects of therapeutic agents, and a screening method which uses the same.

Means for Solving the Problems

As a result, it was found that, by administering reserpine to a mammal, chronic muscle pain and chronic tactile allodynia which is sustained over 1 week or more after its administration can be generated. Further, it was confirmed that this onset of chronic muscle pain and chronic tactile allodynia is originated from decrease of the biogenic amine level caused by reserpine. Further, it was confirmed that the mammal administered with reserpine persistently generates a depressive symptom together with the chronic muscle pain and chronic tactile allodynia. In addition, it was confirmed that pregabalin, duloxetine and pramipexole whose efficacy on fibromyalgia has been confirmed by clinical trials are effective on this disease animal model but diclofenac, which is a non-steroidal anti-inflammatory agent, is not effective.

Thus, the present invention relates to:

[1] A disease animal model, characterized in that a chronic pain is induced by applying, to a mammal, a treatment for reducing the biogenic amine level;

[2] The disease animal model described [1], wherein the chronic pain is chronic muscle pain or chronic tactile allodynia;

[3] The disease animal model described in [1] or [2], which is further accompanied by a depressive symptom;

[4] The disease animal model described in any one of [1] to [3], wherein the treatment for reducing the biogenic amine level is administration of an agent for reducing the biogenic amine level;

[5] The disease animal model described in any one of [1] to [4], wherein the agent for reducing the biogenic amine level is reserpine;

[6] The disease animal model described in any one of [1] to [5], wherein the mammal is a rodent;

[7] The disease animal model described in [6], wherein the rodent is rat; and

[8] The disease animal model described in any one of [1] to [7], wherein the treatment for reducing the biogenic amine level is repeated administration of an agent for reducing the biogenic amine level.

The present invention also relates to:

[9] A method for screening for a therapeutic agent of a chronic pain, characterized in that a test substance is administered to the disease animal model described in any one of [1] to [8];

[10] A method for screening for a therapeutic agent of a chronic pain, characterized in that a test substance is administered to the disease animal model described in any one of [1] to [8], and muscle pressure pain threshold value and/or skin pain sensation threshold value is measured; and

[11] The screening method described in [9] or [10], wherein the chronic pain is fibromyalgia.

Effect of the Invention

By the treatment for decreasing the biogenic amine level, the disease animal model of the present invention persistently expresses chronic pain symptoms of muscle pain and tactile allodynia and expresses a depression symptom as an comorbid symptom. This disease animal model is excellent in the face validity in terms that it shows the sustained chronic pain symptoms (muscle pain and tactile allodynia) and is also accompanied by the depression symptom. Since the biogenic amine such as dopamine, norepinephrine, serotonin and the like is deeply participated in the pain sensation transmission, attenuation of the pain controlling mechanism by the biogenic amine could become a pathophysiological mechanism of the chronic pain. That is, this disease animal model is excellent in the construct validity in terms that reduction of the biogenic amine level of the central nervous system is participated in the pain symptoms. In addition, this disease animal model is also excellent in the predictive validity in terms that the agents whose efficacy on fibromyalgia has been confirmed by clinical trials are effective therein and a mere non-steroidal anti-inflammatory agent is not effective. Thus, said disease animal model is markedly useful as a disease model of chronic pains, particularly fibromyalgia. Accordingly, candidates for therapeutic agent of chronic pains, particularly fibromyalgia, can be efficiently evaluated by the present invention.

BEST MODE OF CARRYING OUT THE INVENTION

Figure 1:
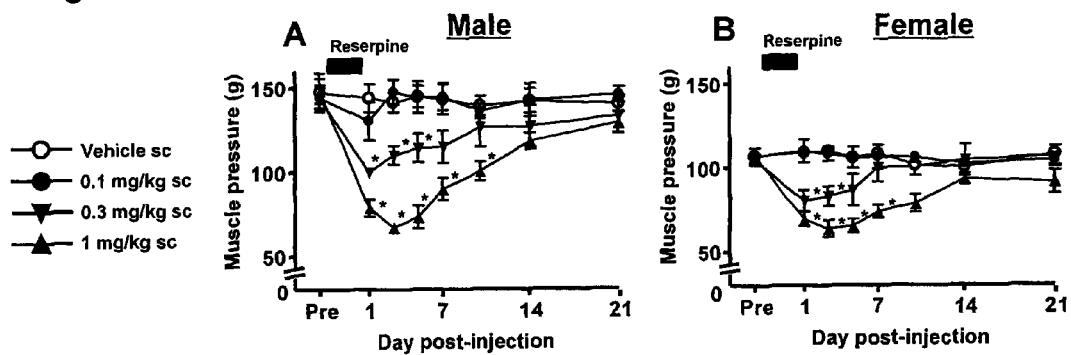
FIG. 1 is a graph showing influence of reserpine repeated administration upon muscle pressure pain threshold value in male rat (A) and female rat (B).

The following describes the present invention further in detail.

As the mammal to be used in the present invention, a small mammal is preferable, and examples thereof include rodents such as rat, mouse, Mongolian gerbil, rabbit, guinea pig, hamster and the like.

However, this is not limited to small mammals and large mammals such as dog, monkey and the like may also be used. Male or female, weeks of age, body weight, the presence or absence of delivery and the like of mammals are not particularly limited as long as they may be employed in the preparation of the disease animal model of interest and in the screening of a test substance.

The amine is a general term of compounds in which the hydrogen atom of ammonia ($NH_3$) is substituted with a hydrocarbon group such as an alkyl group and the like. The biogenic amine means an amine biosynthesized in vivo, and examples thereof include a catecholamine, an indoleamine and an imidazoleamine. Examples of the catecholamine include dopamine, norepinephrine (noradrenaline) and epinephrine (adrenaline). Examples of the indoleamine include serotonin and melatonin. Examples of the imidazoleamine include histamine.

The treatment for reducing the biogenic amine level is a treatment for reducing the amine level in a mammal, and examples thereof include administration of an agent which reduces the biogenic amine level. Examples of the agent which reduces the biogenic amine level include a vesicular monoamine transporter inhibitor, a sympathetic nerve inhibitor, an biogenic amine biosynthesis inhibitor and a neurotoxin. Examples of the vesicular monoamine transporter inhibitor include reserpine and tetrabenazine. Examples of the sympathetic nerve inhibitor include guanethidine, bretylium and α-methyldopa. Examples of the biogenic amine biosynthesis inhibitor include p-chlorophenylalanine, α-methyltyrosine and carbidopa. Examples of the neurotoxin include 6-hydroxydopamine (6-OHDA), 5,7-dihydroxytriptamine (5,7-DHT) and N-(chloroethyl)-N-ethyl-2-bromobenzylamine (DSP-4).

The method for administering an agent which reduces the biogenic amine level is optionally adjusted in accordance with the species and bodyweight of the animal and properties of the agent. The administration may be either single administration or repeated administration (administration of two or more times by making room for a certain period of time). For example, in the case of the repeated administration, the administration may be carried out once or two or more times a day for 2 days to 1 month. The route of administration includes subcutaneous administration, intraperitoneal administration, oral administration and the like, though not limited thereto. The dose is optionally adjusted in accordance with the species and body weight of the animal, route of administration, properties of the agent and the like. For example, from 0.3 mg/kg to 1 mg/kg is preferable when reserpine is subcutaneously administered repeatedly to rat once a day for 3 days. Also, from 1 mg/kg to 3 mg/kg is preferable in the case of single administration of reserpine to rat. As the administration solvent, water, physiological saline and the like may be used, though not limited thereto. The administration may be carried out using a syringe and the like, though not limited to this method.

The chronic pain is a pain which is complained by a patient regardless of exceeding the period of time generally required for healing of the disease or a pain related to progressive non-cancerous diseases. Though the chronic pain continues generally for 3 to 6 months or more in the case of human, it is not appropriate to apply the duration of pain of human as such to other mammals which have life spans different from human. In the case of rodents having a life span of approximately 1 to 3 years, a pain which is generally sustained for several days or more may be regarded as a chronic pain.

The chronic pain in the disease animal model of the present invention may be evaluated by a muscle pressure pain threshold value which is an index of the chronic muscle pain and/or by the reduction of a skin pain sensation threshold value that is an index of tactile allodynia. In addition, the chronic pain can also be evaluated by the reduction of reaction threshold value for a mechanical stimulation such as a plantar stimulation by a Randall-Selitto and a pinch stimulation, reduction of reaction threshold for a thermal stimulation, reduction of reaction threshold for cold stimulation, reduction of reaction threshold for electric stimulation, increase of pain behavior for chemical stimulation, increase of spontaneous pain behavior such as foot lifting behavior in the absence of a stimulation and the like. However, evaluation methods of chronic pains are not limited thereto.

For example, the chronic pain can be evaluated by the measurement of one or two or more a muscle pressure pain threshold value which becomes the index of the chronic muscle pain; reduction of a skin pain sensation threshold value that becomes the index of tactile allodynia; cold sensitivity that becomes the index of cold allodynia; and heat sensitivity that becomes the index of thermal hyperalgesia.

The muscle pressure pain threshold value is a size of minimum pressure stimulation at which an animal generates a withdrawal reaction when a gradually increasing pressure stimulation is applied to a muscle, and as its measurement, various conventionally known methods may be used by selecting them in accordance with the species of animal. For example, in the case of rat, it can be measured by the method of Schafers et al. as is shown later in the Examples, that is, the size of minimum pressure stimulation to which the rat shows a withdrawal reaction is used as the muscle pressure pain threshold value, by adding a gradually increasing pressure stimulation to the right hind leg gastrocnemius muscle.

The skin pain sensation threshold value is size of minimum tactile stimulation at which an animal generates a withdrawal reaction when a gradually increasing tactile stimulation is applied to the skin, and as its measurement, various conventionally known methods may be used by selecting them in accordance with the species of animal. For example, in the case of rat, by the von Frey hair method as is shown later in the Examples, von Frey filaments having different diameters are applied to the plantar surface of the right hind paw by the von Frey hair method as is shown later in the Examples, and the filament of minimum diameter to which the rat shows a withdrawal reaction is measured as the skin pain threshold value.

The cold sensitivity is the reactivity of an animal when a cold stimulus is added thereto, and as its measurement, various conventionally known methods may be used by selecting them in accordance with the species of animal. For example, in the case of rat, as is shown later in Examples, it may be measured as the number of reactions when acetone is applied to the hind legs of the rat by the acetone method.

The heat sensitivity is the reactivity of an animal when a heat stimulus is added thereto, and as its measurement, various conventionally known methods may be used by selecting them in accordance with the species of animal. For example, in the case of rat, as is shown later in Examples, it may be measured by the method of Hargreaves et al., as the hind paw withdrawal reaction concealment when hind paw of a rat is stimulated with infrared heat.

On the other hand, the depressive symptom may be evaluated using, as the index, increase of immobility time in forced swimming test. However, the measurement of depressive symptom is not limited to this index, and in addition to this, immobility time in tail suspension test, spontaneous motor activity and the like may also be used as the index.

In the screening method of the present invention, administration of a test substance may be carried out at any time after the treatment for reducing the biogenic amine level. For example, it is administered within 1 week after completion of the treatment. For example, effect of a test substance may be evaluated by administering it during an optional period of from the $3^{rd}$ day to $7^{th}$ day after the repeated administration of reserpine to a rodent, during which the muscle pressure pain threshold value and skin pain sensation threshold value are significantly reduced (Example 1) and the immobility time in forced swimming test as the index of depressive symptom is significantly reduced (Example 3). In addition, its effect may be evaluated by administering the test substance during an optional period of from the $2^{nd}$ day to $10^{th}$ day after single administration of reserpine to a rodent, during which the muscle pressure pain threshold value, skin pain sensation threshold value and the cold sensitivity are significantly accelerated (Example 5).

As the test substance, a conventionally known or novel synthetic compound, a natural product, an antibody, a nucleic acid, a peptide, a protein and the like, as well as a biological tissue extract, a cell culture supernatant and the like, may be used.

Administration of a test substance is carried out in accordance with the characteristics of the test substance, by oral administration, intravenous administration, percutaneous administration, intraperitoneal administration, intrathecal administration, intracerebroventricular administration and the like. The test substance is generally administered using an administration solvent. For example, when the test substance is orally administered, preferred is a method in which it is dissolved or suspended in water, an organic solvent or the like and forcedly administered using a syringe, a dropper or the like.

In carrying out the screening method of the present invention, it is desirable to use a control group in which physiological saline, distilled water or the like alone instead of the test substance, as a comparative control group to which the-substance-administered group is compared.

EXAMPLES

The following describes the present invention further in detail based on the examples, though the present invention is not limited to these examples.

Example 1

Influence of Repeated Administration of Reserpine Upon the Muscle Pressure Pain Threshold Value and Skin Pain Sensation Threshold Value 1. Test Methods Male and female Sprague-Dawley rats (Japan SLC, Hamamatsu, Japan) were used.

Measurement of muscle pressure pain threshold value was carried out in accordance with the method of Schafers et al. (Schafers M. et al., Pain, 104, 579-588, 2003). A pressure stimulus of gradually increasing to 250 g at the maximum was added to the rat right hind leg gastrocnemius muscle. Size of the minimum pressure stimulus, at which rat shows withdrawal reaction from the right hind leg pressure stimulus, was measured as the muscle pressure pain threshold value (g). The measurement was carried out 3 times at each point of time of the measurement, and the average was used as the measurement value. Measurement of the skin pain sensation threshold value was carried out in accordance with the method of Chaplan et al. (Chaplan et al., J. Neurosci. Methods, 53, 55-63, 1994). This was measured using a series of von Frey filaments having different diameters which may add a constant pressure. After adaptation of each rat to a wire mesh bottom cage for measurement, von Frey filament (0.42, 0.74, 1.2, 2.1, 3.5, 6.0, 9.3 or 15.8 g) was applied to the plantar surface of the right hind paw of the rat until withdrawal reaction occurred on the right hind paw or the reaction did not occur with a lapse of 6 seconds. The von Frey filament was applied using the up and down method. That is, by firstly applying a filament of middle diameter, a filament having one rank smaller diameter was applied when the withdrawal reaction was observed or a filament having one rank larger diameter was applied when the withdrawal reaction was not observed. The skin pain sensation threshold value at each point of time of the measurement was calculated as a hind paw withdrawal reaction threshold value (g) using the calculation formula reported by Chaplan et al. (Chaplan et al., described above). Influences of reserpine upon the muscle pressure pain threshold value and skin pain sensation threshold value were examined by the following protocol. A total of 24 animals for each of male and female rats were used. After measuring muscle pressure pain threshold value and skin pain sensation threshold value before the reserpine treatment (base line), they were divided based on the reserpine administration doses into a solvent (0.5% acetic acid aqueous solution) group, a reserpine 0.1 mg/kg group, a 0.3 mg/kg group and a 1 mg/kg group (the number of animals per one group was 6). The solvent or reserpine was subcutaneously administered on the back of the rats of each group once a day for 3 days. All of the administration volume of the solvent or reserpine was set to 1 ml per 1 kg body weight of each animal. After final administration of the solvent or reserpine, the muscle pressure pain threshold value and skin pain sensation threshold value of each rat were measured 1, 3, 5, 7, 10, 14 and 21 days thereafter. Measurement of muscle pressure pain threshold value and skin pain sensation threshold value was carried out by the experimenters who did not know reserpine administration doses to the animals.

All of the measured values were expressed as average value±standard error. Statistical significance test of the measured values between the reserpine administration groups and the solvent administration group at each point of time was carried out by a two-way analysis of variance and the Bonferroni method. Probability value (P) of less than 5% was judged as statistically significant (P<0.05 was expressed as * in the graphs).

2. Results (1) Muscle Pressure Pain Threshold Value

The results in males and females are respectively shown in FIG. 1A and FIG. 1B. The reserpine treatment significantly reduced the muscle pressure pain threshold value in both of male and female rats (two-way analysis of variance). The muscle pressure pain threshold value was markedly reduced in the reserpine 1 mg/kg group. In comparison with the solvent group, the muscle pressure pain threshold value in the reserpine 1 mg/kg group was statistically significantly low until 10 days after the reserpine final administration in male rats, and until 7 days after the reserpine final administration in female rats (two-way analysis of variance and Bonferroni method).

The above results revealed that the repeated subcutaneous administration of 1 mg/kg reserpine once a day for 3 days induces sufficient and persistent reduction of muscle pressure pain threshold value in male and female rats. This persistent muscle pain inducing pharmacological action of reserpine has not been reported until now but was newly found by this example.

(2) Skin Pain Sensation Threshold Value

Figure 2:
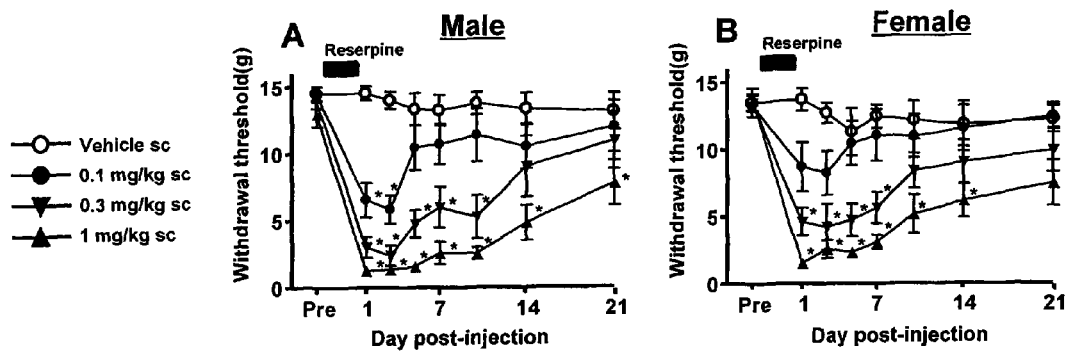
FIG. 2 is a graph showing influence of reserpine repeated administration upon skin pain sensation threshold value in male rat (A) and female rat (B).

The results in males and females are respectively shown in FIG. 2A and FIG. 2B. The reserpine treatment significantly reduced the skin pain sensation threshold value in both of male and female rats (two-way analysis of variance). The skin pain sensation threshold value was markedly reduced in the reserpine 1 mg/kg group. In comparison with the solvent group, the skin pain sensation threshold value in the reserpine 1 mg/kg group was statistically significantly low until 21 days after the reserpine final administration in male rats, and until 14 days after the reserpine final administration in female rats (two-way analysis of variance and Bonferroni method).

The above results revealed that the repeated subcutaneous administration of 1 mg/kg reserpine once a day for 3 days induces sufficient and persistent reduction of skin pain sensation threshold value in male and female rats (tactile allodynia: a pain generated by a tactile stimulus which does not generally cause pain). This pharmacological action of reserpine to persistently reduce skin pain sensation threshold value has not been reported until now but was newly found by this example. That is, since the chronic pain symptoms of consistent muscle pain and tactile allodynia are generated, the above results of (1) and (2) showed that this disease animal model is excellent from the viewpoint of face validity.

Example 2

Influences of the Repeated Administration of Reserpine Upon the Amounts of Dopamine, Norepinephrine and Serotonin in the Spinal Cord, Thalamus and Prefrontal Cortex 1. Test Methods Male Sprague-Dawley rats (7 weeks old, Japan SLC, Hamamatsu, Japan) were used as the animal.

A total of 96 rats were divided into 8 test schedules (collection of samples before administration and 1, 3, 5, 7, 10, 14 or 21 days after the final administration) and further divided each of them into a vehicle (0.5% acetic acid aqueous solution) administration group, a reserpine 0.1 mg/kg administration group, a 0.3 mg/kg administration group and a 1 mg/kg administration group, to 3 rats per group. As shown in Example 1, the vehicle or 0.1, 0.3 or 1 mg/kg of reserpine was repeatedly administered to each rat once a day for 3 days, and the brain and spinal cord were quickly collected 1, 3, 5, 7, 10, 14 or 21 days after the final administration. The thalamus and prefrontal cortex were separated from the brain on an ice-cold dish.

Regarding the sampling before administration, samples were collected before beginning of the repeated administration of vehicle or reserpine. The collected samples were quickly frozen and stored at −80° C. until their use in the measurements. On the day of the measurement, tissues of respective samples were subjected to wet weight measurement, homogenized in 0.2 M perchloric acid/0.1 mM EDTA-2Na solution using an ultrasonic homogenizer. After centrifugation at 15,000 g and at 4° C. for 15 minutes, the supernatant was adjusted to pH 3.5 using sodium acetate and filtered using a filter. Amounts of dopamine, norepinephrine and serotonin in these samples were measured using a high performance liquid chromatography (column: SC-50DS 30, 150 mm, Eicom Co., Ltd., Kyoto, Japan, mobile phase composition: 0.1 M sodium acetate buffer, 0.1 M citrate buffer, pH 3.5, 5 mg/l EDTA-2Na, 190 mg/l sodium octane sulfonic acid, 17% methanol) and an electrochemical detector (ECD-300, Eicom Co., Ltd., Kyoto, Japan). The measurement was carried out under conditions of flow rate 0.5 ml/min, applied voltage 750 mV and 25° C. Amounts of dopamine, norepinephrine and serotonin in the samples were quantified by comparing sample peak areas of respective standards measured on the same day of the sample measurement. All of the measured values were expressed as average value±standard error in the graphs, and unit of the measured values was set to ng/g tissue wet weight.

Statistical difference of the measured values between the reserpine administration group and the vehicle administration group in each test schedule was carried out by the two-way analysis of variance and the Bonferroni method. Probability value (P) of less than 5% was judged as statistically significant (P<0.05 was expressed as * in the graphs). In addition, average values of respective groups at each point of time were expressed as percentages of the average values of corresponding vehicle administration groups.

2. Results

Figure 3:
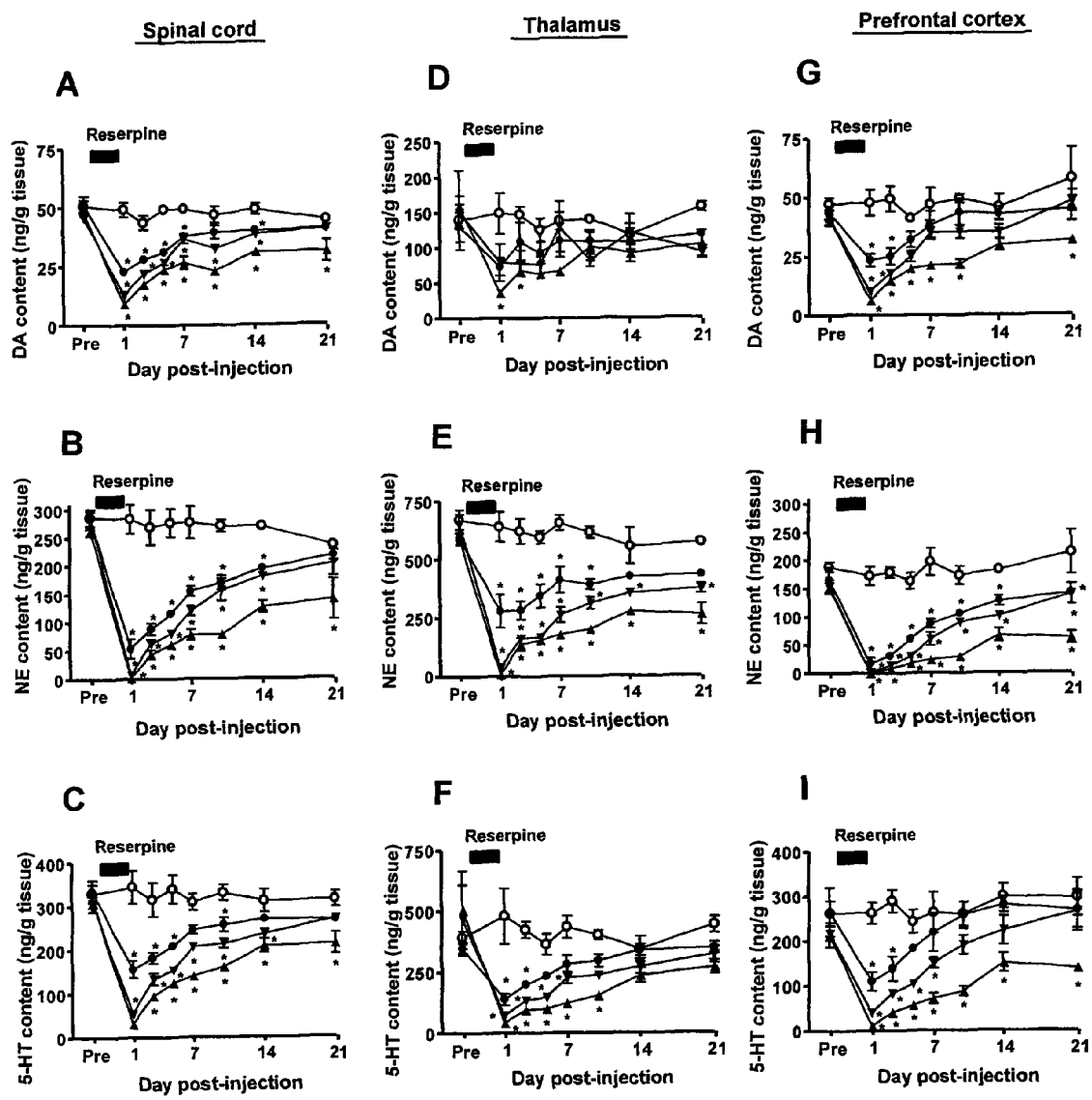
FIG. 3 is a graph respectively showing influences of the reserpine repeated administration treatment upon the amounts of dopamine (A, D and G), norepinephrine (B, E and H) and serotonin (C, F and I) in the spinal cord, thalamus and prefrontal cortex (open circle: vehicle administration group, closed circle: 0.1 mg/kg administration group, closed inverted triangle, 0.3 mg/kg administration group, closed triangle: 1 mg/kg administration group).
Figure 4:
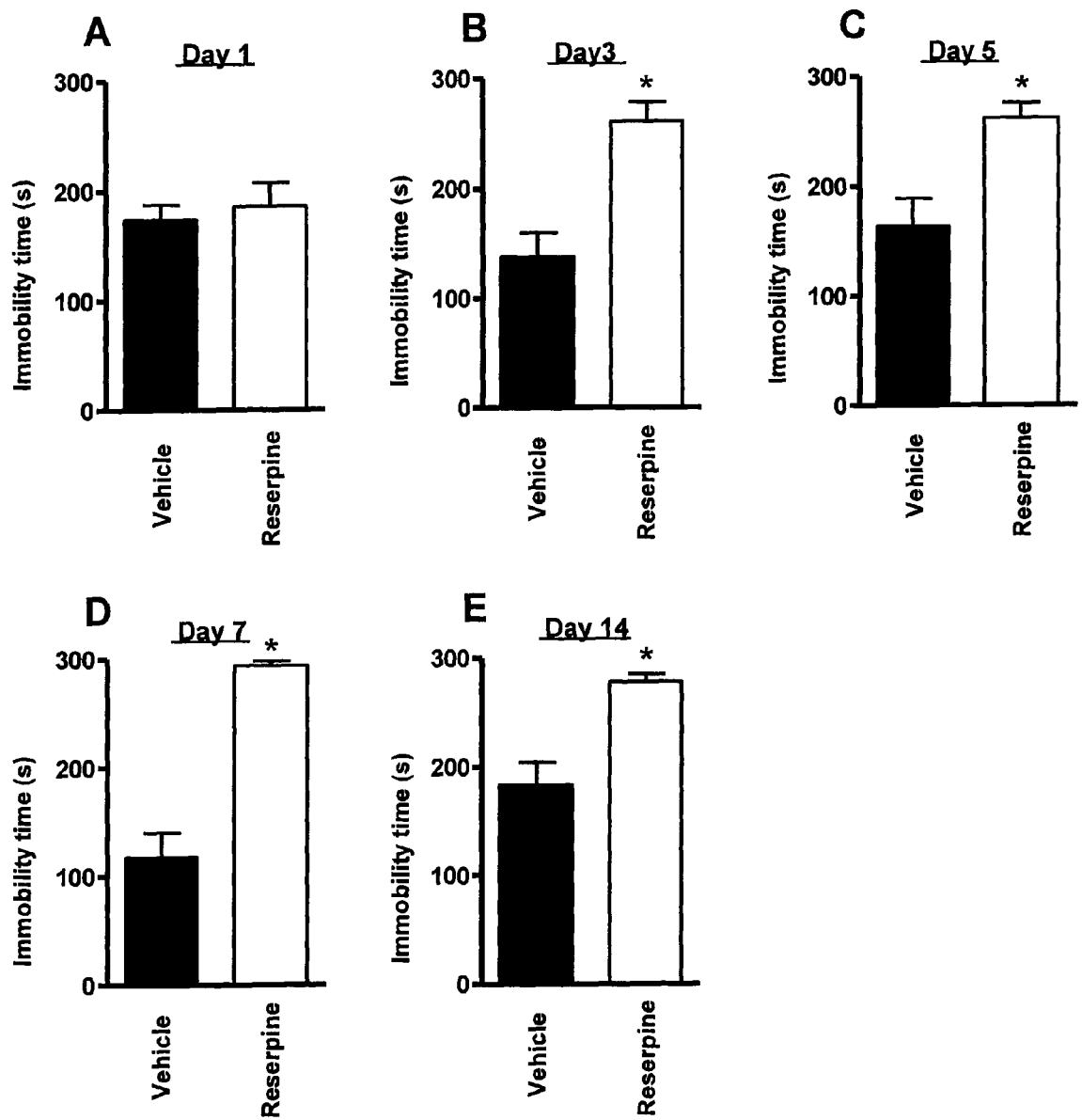
FIG. 4 is a graph showing immobility time in a forced swimming test on the $1^{st}$ day (A) $3^{rd}$ day (B), $5^{th}$ day (C), $7^{th}$ day (D) and $14^{th}$ day (E) after repeated administration of reserpine.

Effects of the administration of reserpine on the amounts of dopamine, norepinephrine and serotonin in the spinal cord are respectively shown in FIG. 3A, FIG. 3B and FIG. 3C, effects of the administration of reserpine on the amounts of dopamine, norepinephrine and serotonin in the thalamus are respectively shown in FIG. 3D, FIG. 3E and FIG. 3F, and effects of the administration of reserpine on the amounts of dopamine, norepinephrine and serotonin in the prefrontal cortex are respectively shown in FIG. 3G, FIG. 3H and FIG. 3I.

In the spinal cord, by the administration of 0.1, 0.3 and 1 mg/kg of reserpine, the amount of dopamine 1 day thereafter was reduced to 46.4%, 26.3% and 18.4% of the vehicle administration group, and all of which were significant reduction compared to the vehicle administration group. In the same manner, the amount of norepinephrine was reduced to 19.1%, 2.6% and 0.6%, and all of which were significant reduction. Also, the amount of serotonin was reduced to 45.4%, 15.7% and 0.1%, and all of which were significant reduction. Thereafter, amounts of the dopamine, norepinephrine and serotonin were gradually increased. However, amounts of the dopamine, norepinephrine and serotonin after 21 days in the reserpine 1 mg/kg administration group were 70.1%, 59.4% and 67.8%, respectively, of the vehicle administration group, and all of which were significantly low compared to the vehicle administration group. That is, it was revealed that the repeated administration of 1 mg/kg of reserpine once a day for 3 days markedly and persistently reduces amounts of dopamine, norepinephrine and serotonin in the rat spinal cord.

In the thalamus, by the administration of 0.1, 0.3 and 1 mg/kg of reserpine, the amount of dopamine 1 day thereafter was reduced to 49.2%, 53.2% and 24.5% of the vehicle administration group, and all of which were significant reduction compared to the vehicle administration group. In the same manner, the amount of norepinephrine was reduced to 43.8%, 6.1% and 1.2%, and all of which were significant reduction. Also, the amount of serotonin was reduced to 28.8%, 14.8% and 8.9%, and all of which were significant reduction. Thereafter, all of the amounts of dopamine, norepinephrine and serotonin were gradually increased. However, amounts of dopamine, norepinephrine and serotonin after 21 days in the reserpine 1 mg/kg administration group were 66.5%, 46.0% and 60.7%, respectively, of the vehicle administration group, and all of which were significantly lower compared to the vehicle administration group. That is, it was revealed that the repeated administration of 1 mg/kg of reserpine once a day for 3 days markedly and persistently reduces amounts of dopamine, norepinephrine and serotonin in the rat thalamus.

In the prefrontal cortex, the administration of 0.1, 0.3 and 1 mg/kg of reserpine, the amount of dopamine 1 day thereafter was reduced to 49.1%, 21.4% and 13.4% of the vehicle administration group, and all of which were significant reduction compared to the vehicle administration group. In the same manner, the amount of norepinephrine was reduced to 10.2%, 0.7% and 0.2%, and all of which were significant reduction. Also, the amount of serotonin was reduced to 42.0%, 15.5% and 4.6%, and all of which were significant reduction. Thereafter, all of the amounts of dopamine, norepinephrine and serotonin were gradually increased. However, amounts of the dopamine, norepinephrine and serotonin after 21 days in the reserpine 1 mg/kg administration group were 54.9%, 29.1% and 47.0%, respectively, of the vehicle administration group, and all of which were significantly lower compared to the vehicle administration group. That is, it was revealed that the repeated administration of 1 mg/kg of reserpine once a day for 3 days markedly and persistently reduces amounts of dopamine, norepinephrine and serotonin in the rat prefrontal cortex.

Dopamine, norepinephrine and serotonin are involved in the pain sensation transmission, and all of the spinal cord, thalamus and prefrontal cortex are the main regions responsible for the pain sensation transmission. Accordingly, these results show that the reduction of muscle pressure pain threshold value and the reduction of skin pain sensation threshold value shown in Example 1 are induced by the reduction of the biogenic amine level in the regions related to pain sensation transmission pathway. That is, it was shown that this disease animal model is excellent in the construct validity from the viewpoint that reduction of the biogenic amine level in the central nervous system associated with the pain transmission is involved therein as a pain pathogenesis mechanism.

Example 3

Influence of Repeated Administration of Reserpine Upon Immobility Time in Forced Swimming Test 1. Test Methods Male Sprague-Dawley rats (7 weeks old, Japan SLC, Hamamatsu, Japan) were used as the animal. The forced swimming test was carried out by modifying the method of Porsolt et al. (1977) in the following manner. A soft wire equipped with a magnet (1 mm in diameter, 3 mm in length) was attached to both forelimbs of each animal, and the animal was allowed to swim in a cylindrical plastic water bath (20 cm in diameter, 45 cm in height) filled with water (24±1° C.) to a depth of 30 cm. In this test, the immobility time of each animal was measured using a forced swimming automatic measuring device (MicroAct Scratching Test version 1.06; Neuroscience, Tokyo, Japan) which detects movement of the forelimbs equipped with the magnet, through a coil around the cylinder.

Influence of reserpine upon the immobility time in the forced swimming test was examined in accordance with the following protocol. A total of 80 rats were divided into 5 test schedules (measurement of immobility time after 1, 3, 5, 7 or 14 days of the final administration) and further divided each of them into a vehicle (0.5% acetic acid aqueous solution) administration group and a reserpine 1 mg/kg administration group, to 8 rats per group. As shown in Example 1, the vehicle or 1 mg/kg of reserpine was repeatedly administered subcutaneously once a day for 3 days. One forced swimming test included a pretest session (15 minutes of swimming) and a test session (5 minutes of swimming) 24 hours after the pretest session, and measurement of the immobility time was carried out in the test session. The pretest session was carried out after 0 (i.e., just after the final administration), 2, 4, 6 and 13 days of the final administration of the vehicle or reserpine, and the test session was carried out after 1, 3, 5, 7 and 14 days of the final administration of the vehicle or reserpine. Each rat was subjected to only one forced swimming test. All of the measured values were expressed as average value±standard error. Statistical difference of the measured values between the reserpine administration groups and the vehicle administration group in each test schedule was carried out by the Student's t-test. Probability value (P) of less than 5% was judged as statistically significant (P<0.05 was expressed as * in the graphs).

2. Results

Results of the forced swimming tests after 1, 3, 5, 7 and 14 days of the final administration of reserpine are shown in FIG. 4A, FIG. 4B, FIG. 4C, FIG. 4D and FIG. 4E, respectively. Significant increase in the immobility time by the reserpine administration was not found after 1 day of the final administration (P=0.625, Student's t-test). On the other hand, the reserpine administration group showed significant increase in the immobility time compared to the vehicle administration group after 3, 5, 7 and 14 days of the final administration (respectively P=0.0007, P=0.004, P<0.0001 and P=0.0008, Student's t-test). The above results show that the repeated administration of 1 mg/kg of reserpine once a day for 3 days induces a depressive symptom at least during the period of 3 to 14 days of the final administration. Since it is well known that fibromyalgia patients exhibit depression as a comorbid symptom at a high rate, it is shown that the disease animal model has a high similarity with the fibromyalgia patients from the viewpoint that it exhibits a depressive symptom as a comorbid symptom. That is, it was shown that the disease animal model is excellent from viewpoint of face validity because the pain symptom was accompanied by a depressive symptom.

Example 4

Evaluation of Effects of Drugs on Reserpine Repeated Administration-Induced Reduction of Muscle Pressure Pain Threshold Value and Skin Pain Sensation Threshold Value 1. Test Methods Male Sprague-Dawley rats (Japan SLC, Hamamatsu, Japan) were used as the animal. A total of 30 rats were used for each drug. As shown in Example 1, 1 mg/kg of reserpine was repeatedly administered subcutaneously on the back of 24 rats once a day for 3 days to induce reduction of the muscle pressure pain threshold value and skin pain sensation threshold value. The other 6 rats were subjected to the test as a healthy control group without carrying out the reserpine treatment.

All of the evaluations of drug effects were carried out 5 days after the final administration of reserpine. At this timing, reduction of the muscle pressure pain threshold value and reduction of the skin pain sensation threshold value were remarkable and statistically significant levels (Example 1) and the immobility time at the time of forced swimming test, as the index of a depressive symptom, was significantly prolonged in comparison with the control group (Example 3).

On the day of drug effect evaluation (5 days after the final administration of reserpine), the muscle pressure pain threshold value and skin pain sensation threshold value were firstly measured on all of the rats (24 reserpine-treated rats and 6 healthy rats). The 24 reserpine-treated rats were divided into 4 groups based on the doses of the test drug, and the muscle pressure pain threshold value and skin pain sensation threshold value were measured after 30, 60, 120 or 240 minutes of the drug or solvent administration. On the 6 healthy rats, the drug administration was not carried out, but only the measurement of muscle pressure pain threshold value and skin pain sensation threshold value was carried out. The measurement of drug effects was carried out by experimenters who did not know the doses of drug treatment of animals. The solvents, administration doses and routes of administration of respective test drugs are shown in the following table

| Test drug | Solvent | Route of administration | Administration dose |
|---|---|---|---|
| Pregabalin | Distilled water | Oral administration | 0, 3, 10, 30 mg/kg |
| Duloxetine | Distilled water | Oral administration | 0, 3, 10, 30 mg/kg |
| Pramipexole | Physiological saline | Subcutaneous administration | 0. 0.1, 0.3, 1 mg/kg |
| Diclofenac | 0.5% methyl cellulose | Oral administration | 0, 1, 3, 10 mg/kg |

All of the measured values were expressed as average value±standard error. Statistical significance test of the measured values between the test drug administration groups and the solvent administration group at each point of time was carried out by a two-way analysis of variance and the Bonferroni method. Probability value (P) of less than 5% was judged as statistically significant (P<0.05 was expressed as * in the graphs).

2. Results

Figure 5:
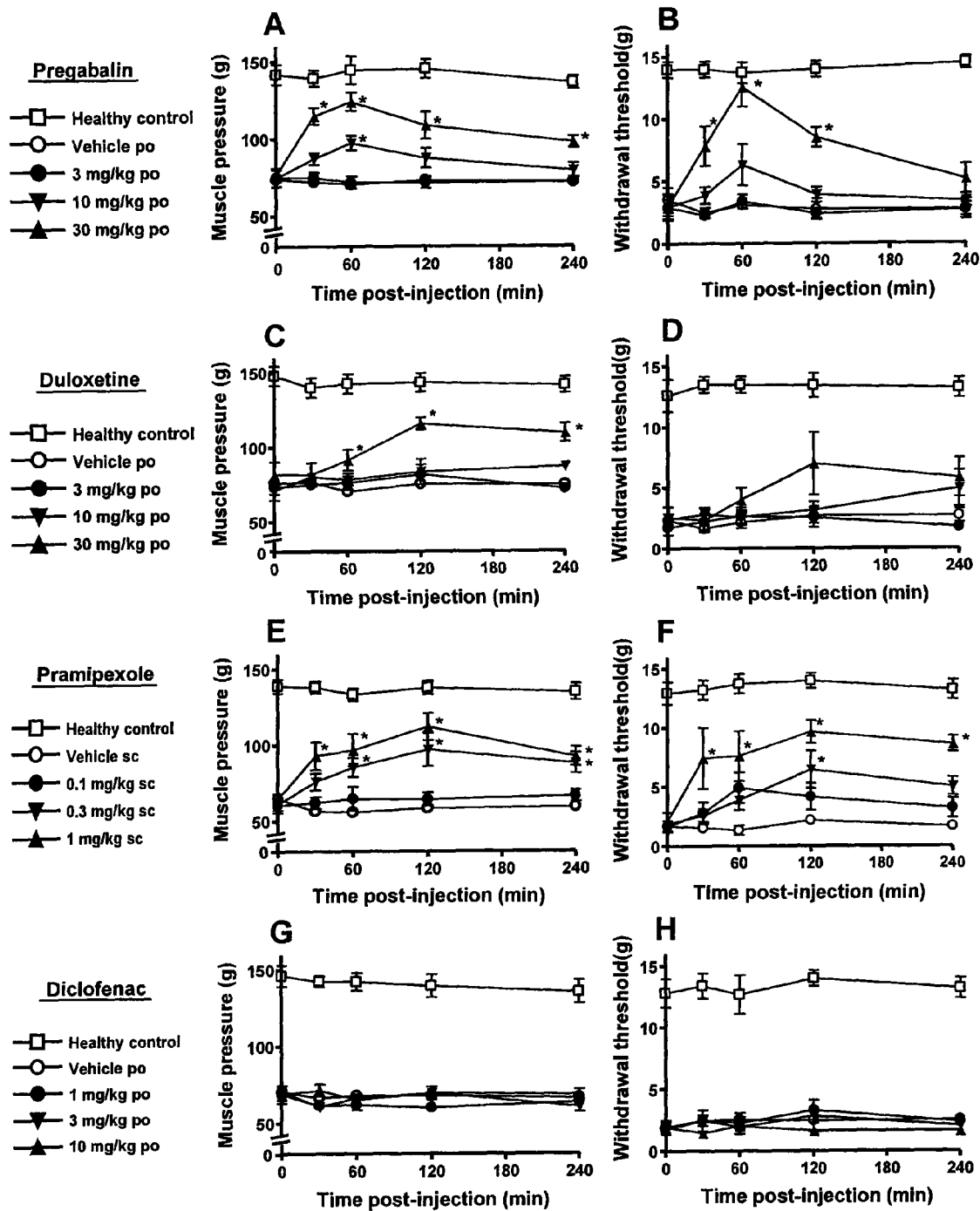
FIG. 5 is a graph respectively showing effects of pregabalin (A and B), duloxetine (C and D), pramipexole (E and F) and diclofenac (G and H) on the reduction of muscle pressure pain threshold value and reduction of skin pain sensation threshold value, which were induced by repeated reserpine administration.

Effects of pregabalin on the reserpine repeated administration-induced muscle pressure pain threshold value reduction and skin pain sensation threshold value reduction are respectively shown in FIG. 5A and FIG. 5B. Pregabalin dose-dependently recovered the reserpine repeated administration-induced muscle pressure pain threshold value reduction and skin pain sensation threshold value reduction. The effect of pregabalin was statistically significant at a dose of 10 or 30 mg/kg by the index of muscle pressure pain threshold value, and at a dose of 30 mg/kg by the index of skin pain sensation threshold value (two-way analysis of variance and the Bonferroni method). This result shows that the useful effect of pregabalin whose usefulness has been proved by a clinical trial on fibromyalgia patients (Mease P J et al., J. Rheumatol., 35, 502-514, 2008) can be detected by the disease animal model.

Effects of duloxetine on the reserpine repeated administration-induced muscle pressure pain threshold value reduction and skin pain sensation threshold value reduction are respectively shown in FIG. 5C and FIG. 5D. Duloxetine statistically significantly recovered the reserpine repeated administration-induced muscle pressure pain threshold value reduction at a dose of 30 mg/kg (two-way analysis of variance and the Bonferroni method). Duloxetine showed a tendency to recover the reserpine repeated administration-induced skin pain sensation pain threshold value reduction but was not statistically significant (two-way analysis of variance and the Bonferroni method). This result shows that the useful effect of duloxetine whose usefulness has been proved by a clinical trial on fibromyalgia patients (Russell I J et al., Pain, 136, 432-444, 2008) can be detected by the disease animal model.

Effects of pramipexole on the reserpine repeated administration-induced muscle pressure pain threshold value reduction and skin pain sensation threshold value reduction are respectively shown in FIG. 5E and FIG. 5F. Pramipexole dose-dependently recovered the reserpine repeated administration-induced muscle pressure pain threshold value reduction and skin pain sensation threshold value reduction. The effect of pramipexole was statistically significant at a dose of 0.3 or 1 mg/kg by the indexes of muscle pressure pain threshold value and skin pain sensation threshold value (two-way analysis of variance and the Bonferroni method). This result shows that the useful effect of pramipexole whose usefulness has been proved by a clinical trial on fibromyalgia patients (Holman A J and Myers R R, Arthritis Rheum., 52, 2495-2505, 2005) can be detected by the disease animal model.

Effects of a non-steroidal anti-inflammatory agent, diclofenac, on the reserpine repeated administration induced muscle pressure pain threshold value reduction and skin pain sensation threshold value reduction are respectively shown in FIG. 5G and FIG. 5H. Diclofenac up to the dose of 10 mg/kg did not recover the reserpine repeated administration induced muscle pressure pain threshold value reduction and skin pain sensation threshold value reduction. The effect of diclofenac was not statistically significant by the indexes of muscle pressure pain threshold value and skin pain sensation threshold value (two-way analysis of variance and the Bonferroni method). This result is in accordance with the findings that non-steroidal anti-inflammatory agents ibuprofen (Yunus M B et al., J Rheumatol, 16, 527-532, 1989) and naproxen (Goldenberg D L et al., Arthritis Rheum, 29, 1371-1377, 1986) do not have a significant effect in the treatment of fibromyalgia patients, thus showing that the disease animal model does not nonspecifically detect effects of analgesics.

The evaluation results of the above-mentioned four test drugs showed that the disease animal model has a high predictability on the clinical effect of test drugs in the chronic pain disease patients such as of fibromyalgia. That is, the disease animal model is excellent in predictive validity.

Example 5

Influence of Reserpine Single Administration Upon Muscle Pressure Pain Threshold Value, Skin Pain Sensation Threshold Value, Cold Sensitivity and Heat Sensitivity 1. Test Methods Male Sprague-Dawley rats (Japan SLC, Hamamatsu, Japan) were used. Measurement of muscle pressure pain threshold value was carried out in the same manner as in Example 1. That is, a pressure stimulus of gradually increasing to 250 g at the maximum was added to the right hind leg gastrocnemius muscle of each rat. Size of the minimum pressure stimulus, at which rat shows withdrawal reaction from the right hind leg pressure stimulus, was measured as the muscle pressure pain threshold value (g). The measurement was carried out 3 times at each point of time of the measurement, and the average was used as the measurement value.

Measurement of the skin pain sensation threshold value was carried out in the same manner as in Example 1. That is, this was measured using a series of von Frey filaments having different diameter which can add a constant pressure. After adaptation of each rat to a wire mesh bottom cage for measurement, von Frey filament (0.42, 0.74, 1.2, 2.1, 3.5, 6.0, 9.3 or 15.8 g) was applied to the plantar surface of the right hind paw of the rat until withdrawal reaction occurred on the right hind paw or the reaction did not occur within 6 seconds. The von Frey filament was applied using the up and down method. That is, by firstly applying a filament of about middle diameter, a filament having one rank smaller diameter was applied when the withdrawal reaction was observed or a filament having one rank larger diameter was applied when the withdrawal reaction was not observed. The skin pain sensation threshold value at each point of time was calculated as a hind paw withdrawal reaction threshold value (g).

Measurement of cold sensitivity was carried out in accordance with the method of Choi et al. (Choi et al., Pain, 59, 369-376, 1994). After adaptation of each rat to a wire mesh bottom cage for measurement, 50 µl of acetone was sprayed to the plantar surface of the right hind paw of the rat using a syringe for insulin injection. The number of reactions of the right hind paw (flinching, lifting and leg licking) occurred during 1 minute just after the spraying was measured and used as the index of cold sensitivity. At each point of time of the measurement, the acetone spraying was carried out 3 times at 5 minute intervals and the average was used as the measured vale. In this measuring system, larger reaction frequency represents acceleration of the cold sensitivity.

Measurement of the heat sensitivity was carried out by the method of Hargreaves et al. (Hargreaves et al., Pain, 32, 77-88, 1988). A transparent measuring box was put on a glass plate supported with platforms and a rat was put therein and acclimatized. A mobile infrared heat source was arranged under the glass plate and focused on the plantar surface of the right hind paw of the rat. A latency time required for the rat to show a withdrawal reaction of right hind leg from the heat source was measured as a withdrawal latency time and used as the index of heat sensitivity. According to this measuring system, shorter withdrawal latency time represents acceleration of the skin heat sensitivity.

Influences of the reserpine single administration upon the muscle pressure pain threshold value, skin pain sensation threshold value, cold sensitivity and heat sensitivity were examined in accordance with the following protocol. A total of 12 male rats were used. The muscle pressure pain threshold value, skin pain sensation threshold value, cold sensitivity and heat sensitivity before the reserpine treatment (base lines) were measured and then they were divided into a solvent (0.5% acetic acid aqueous solution) group and a reserpine (3 mg/kg) group (the number of animals per group was 6). The solvent or reserpine was subcutaneously administered on the back of the rats of each group. The administration volume of the solvent or reserpine was set to 1 ml per 1 kg animal body weight in all cases. The muscle pressure pain threshold value, skin pain sensation threshold value, cold sensitivity and heat sensitivity of each rat were measured at the points of measurement time of acute phase after administration of the solvent or reserpine (2, 4, 8 and 24 hours) and chronic phase (2, 3, 5, 7, 10, 14 and 21 days). The measurement was carried out by experimenters who did not know the doses of substance administered.

All of the measured values were expressed as average value±standard error. Statistical significance test of the measured values between the reserpine administration groups and the solvent administration group at each point of time was carried out by the two-way analysis of variance and the Bonferroni method. Probability value (P) of less than 5% was judged as statistically significant (P<0.05 was expressed as * in the graphs).

2. Results (1) Muscle Pressure Pain Threshold Value

Figure 6:
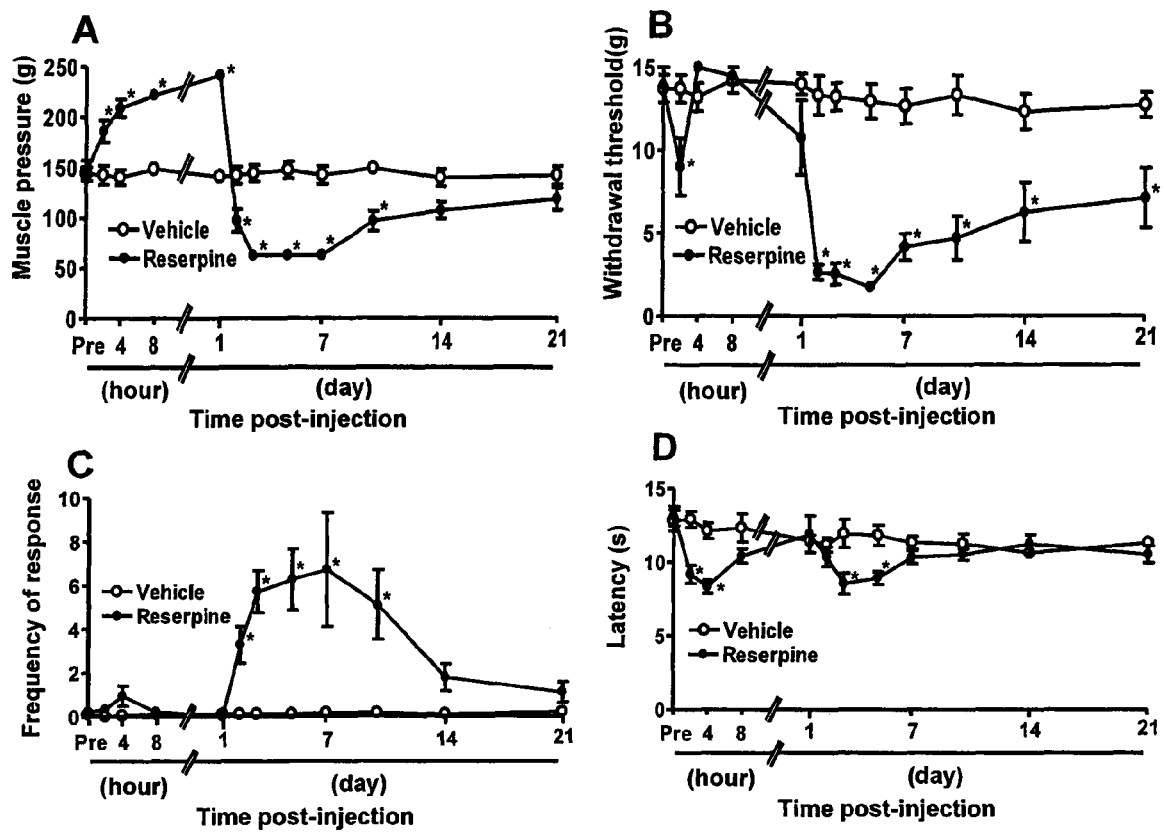
FIG. 6 is a graph showing influences of single administration treatment of reserpine upon muscle pressure pain threshold value (A), skin pain sensation threshold value (B), cold sensitivity (C) and heat sensitivity (D).
Figure 7:
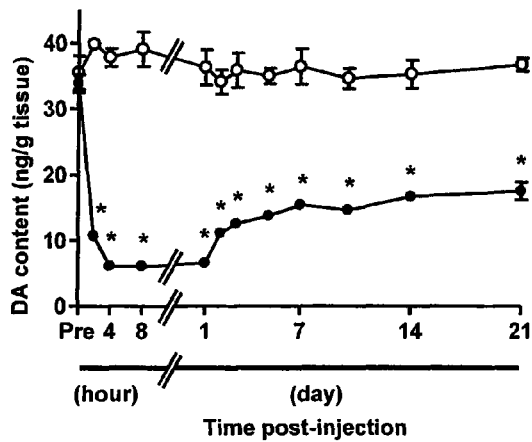
FIG. 7 is a graph respectively showing influences of vehicle single administration (open circle) and reserpine single administration (closed circle) upon the amount of dopamine (A), norepinephrine (B), serotonin (C), DOPAC (D), MHPG (E) and 5-HIAA (F) in the spinal cord.
Figure 7:
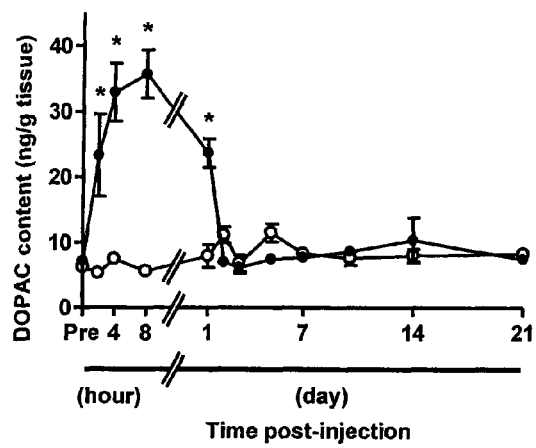
Figure 7:
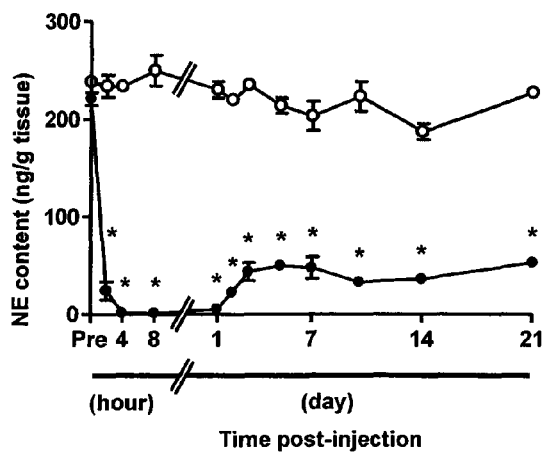
Figure 7:
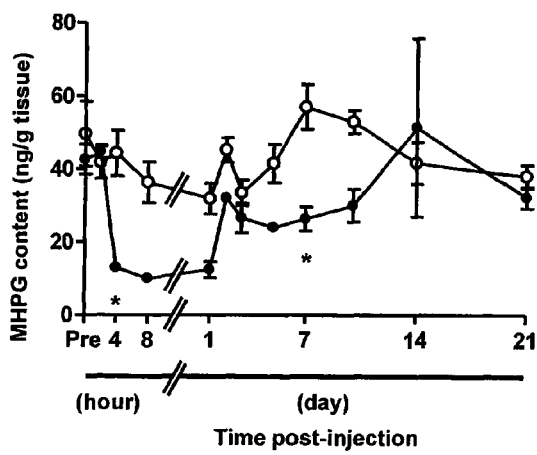
Figure 7:
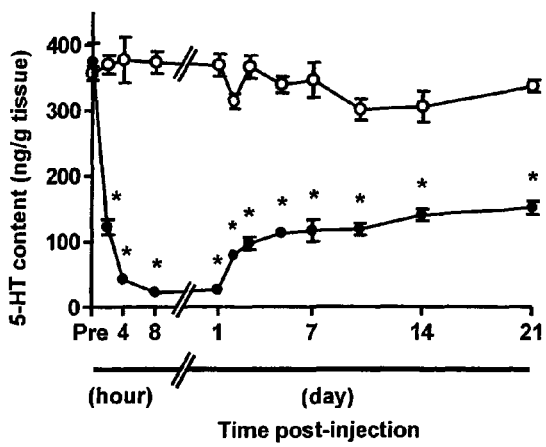
Figure 7:
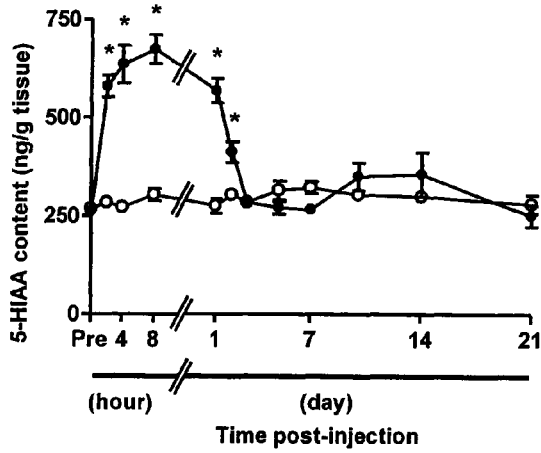
Figure 8:
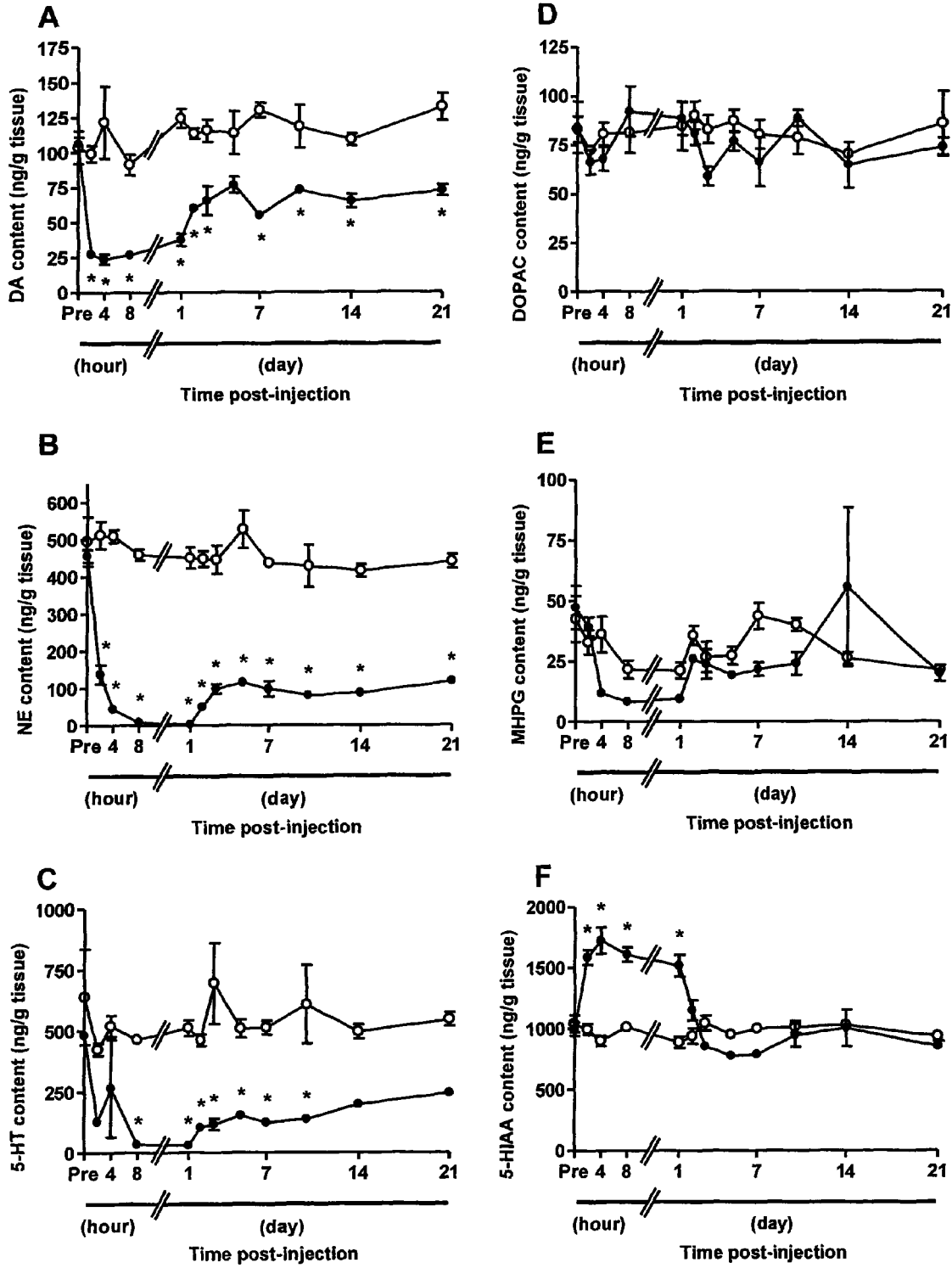
FIG. 8 is a graph respectively showing influences of vehicle single administration (open circle) and reserpine single administration (closed circle) upon the amount of dopamine (A), norepinephrine (B), serotonin (C), DOPAC (D), MHPG (E) and 5-HIAA (F) in the thalamus.
Figure 9:
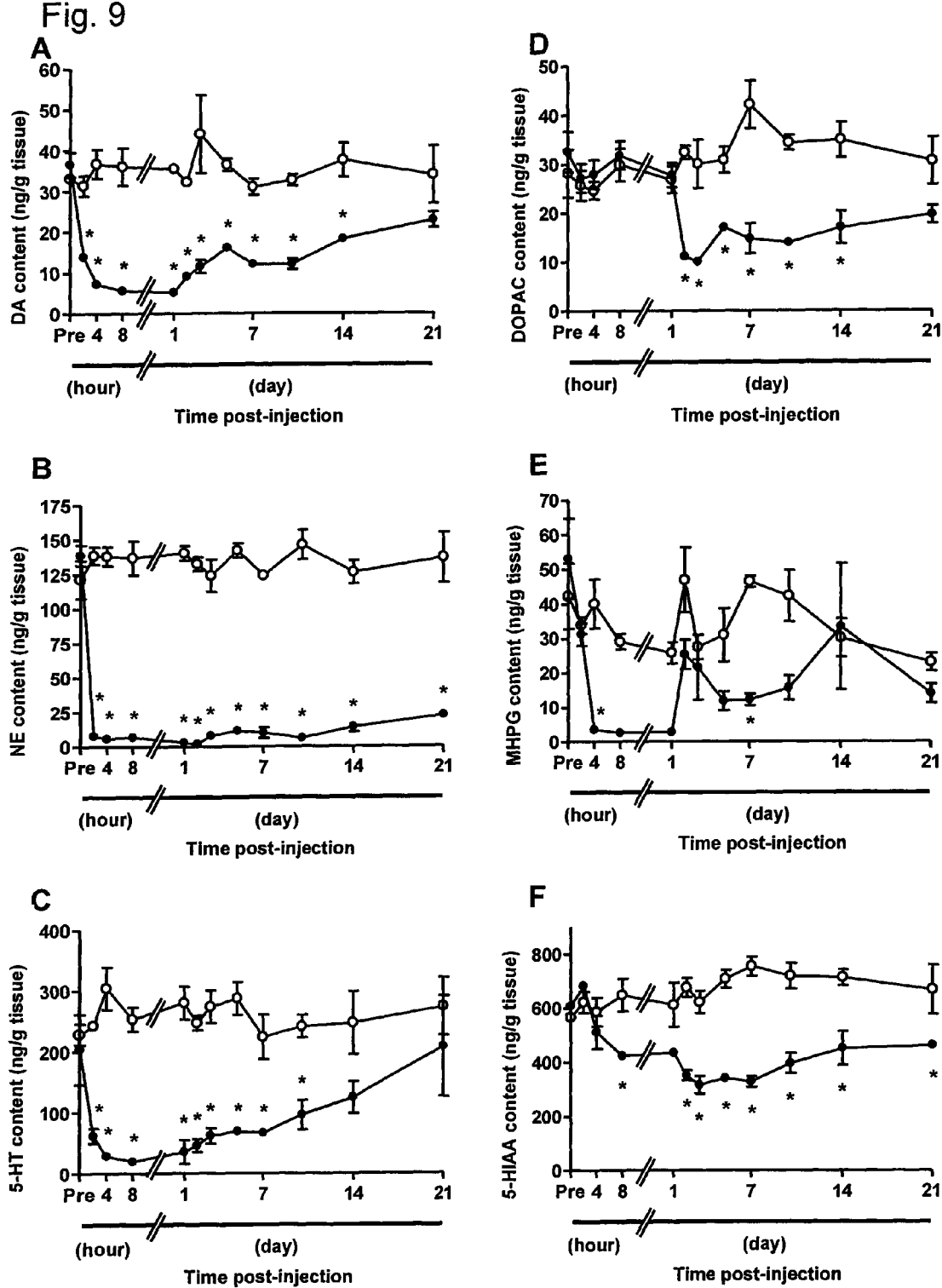
FIG. 9 is a graph respectively showing influences of vehicle single administration (open circle) and reserpine single administration (closed circle) upon the amount of dopamine (A), norepinephrine (B), serotonin (C), DOPAC (D), MHPG (E) and 5-HIAA (F) in the prefrontal cortex.

Timecourse change in the muscle pressure pain threshold value by reserpine single administration is shown in FIG. 6A. Reserpine significantly increased the muscle pressure pain threshold value after 2, 4, 8 and 24 hours of its administration. On the other hand, it significantly reduced the muscle pressure pain threshold value after 2, 3, 5, 7 and 10 days of the administration (two-way analysis of variance and the Bonferroni method). That is, it was revealed that, at the acute phase (within 24 hours after administration) and chronic phase (in and after 2 days of administration), single subcutaneous administration of reserpine induces different changes in the muscle pressure pain threshold value (hyposensitivity at acute phase and hypersensitivity at chronic phase).

(2) Skin Pain Sensation Threshold Value

Timecourse change in the skin pain sensation threshold value by reserpine single administration is shown in FIG. 6B. Reserpine significantly reduced the skin pain sensation threshold value after 2 hours of its administration. Also, reserpine significantly reduced the skin pain sensation threshold value during the chronic phase of 2, 3, 5, 7, 10, 14 and 21 days after its administration (two-way analysis of variance and the Bonferroni method). That is, single subcutaneous administration of reserpine induced a transient (recovers 4 hours after its administration) tactile allodynia during the acute phase (within 24 hours after the administration). It was revealed that this tactile allodynia is once recovered and then recurred during the chronic phase (in and after 2 days of administration) as persistent tactile allodynia.

(3) Cold Sensitivity

Timecourse change in the cold sensitivity by single administration of reserpine is shown in FIG. 6C. Reserpine did not show significant increase in the number of reactions within 24 hours after its administration. On the other hand, it significantly increased the number of reactions after 2, 3, 5, 7 and 10 days of its administration (two-way analysis of variance and the Bonferroni method). That is, it was revealed that single subcutaneous administration of reserpine does not cause a change in cold sensitivity during the acute phase (within 24 hours after administration) but induces acceleration of cold sensitivity during the chronic phase (in and after 2 days of administration)

(4) Heat Sensitivity

Timecourse change in the heat sensitivity by single administration of reserpine is shown in FIG. 6D. Reserpine significantly shortened the latency time in 2 and 4 hours after its administration and 2 and 5 days after the administration (two-way analysis of variance and the Bonferroni method). That is, single subcutaneous administration of reserpine induced a transient (recovers 8 hours after its administration) acceleration of heat sensitivity during the acute phase (within 24 hours after the administration). It was revealed that this acceleration of heat sensitivity is once recovered and then recurred during the chronic phase (in and after 2 days of administration).

Based on the results of Example 5, it was revealed that, in the animals which received the reserpine treatment, a change in the pain sensation threshold value different from the case of acute phase (within 24 hours after administration) is generated during the chronic phase (in and after 2 days of administration) after the reserpine treatment.

Example 6

Influences of Reserpine Single Administration Upon the Amounts of Dopamine, Norepinephrine, Serotonin, 3,4-dihydroxyphenylacetic acid (DOPAC; a Dopamine Metabolite), 3-methoxy-4-hydroxyphenyl ethylene glycol (MHPG; a Norepinephrine Metabolite) and 5-Hydroxyindoleacetic Acid (5-HIAA; a Serotonin Metabolite) in the Spinal Cord, Thalamus and Prefrontal Cortex 1. Test Methods Male Sprague-Dawley rats (7 weeks old, Japan SLC, Hamamatsu, Japan) were used as the animal.

A total of 72 rats were divided into 12 test schedules (collection of samples before the administration, 2, 4, 8 and 24 hours after the administration and 2, 3, 5, 7, 10, 14 and 21 days thereafter) and further divided each of them into a vehicle (0.5% acetic acid aqueous solution) administration group and a reserpine 3 mg/kg administration group, to 3 rats per group. As shown in Example 5, the vehicle or 3 mg/kg of reserpine was administered subcutaneously only once to each rat, and the brain and spinal cord were quickly collected after 2, 4, 8 or 24 hours or 2, 3, 5, 7, 10, 14 or 21 days of the administration. The thalamus and prefrontal cortex were separated from the brain on an ice-cold dish. Regarding the sampling before administration, samples were collected before beginning of the administration of the vehicle or reserpine. The collected samples were quickly frozen and stored at −80° C. until their use in the measurements. On the day of the measurement, tissues of respective samples were subjected to wet weight measurement, homogenized in 0.2 M perchloric acid/0.1 mM EDTA-2Na solution using an ultrasonic homogenizer. After centrifugation at 15,000 g and at 4° C. for 15 minutes, the supernatant was adjusted to pH 3.5 using sodium acetate and filtered using a filter. Amounts of dopamine, norepinephrine, serotonin, DOPAC, MHPG and 5-HIAA in these samples were measured using a high performance liquid chromatography (column: SC-50DS 3.0, 150 mm, Eicom Co., Ltd., Kyoto, Japan, mobile phase composition: 0.1 M sodium acetate buffer, 0.1 M citrate buffer, pH 3.5, 5 mg/l EDTA-2Na, 200 mg/l sodium octane sulfonic acid, 16% methanol) and an electrochemical detector (ECD-300, Eicom Co., Ltd., Kyoto, Japan). The measurement was carried out under conditions of flow rate 0.5 ml/min, applied voltage 750 mV and 25° C. Amounts of dopamine, norepinephrine, serotonin, DOPAC, MHPG and 5-HIAA in the samples were quantified by comparing sample peak areas of respective standards measured on the same day of the sample measurement.

All of the measured values were expressed as average value±standard error in the graphs, and unit of the measured values was set to ng/g tissue wet weight. Statistical difference of the measured values between the reserpine administration group and the vehicle administration group in each test schedule was carried out by the two-way analysis of variance and the Bonferroni method. Probability value (P) of less than 5% was judged as statistically significant (P<0.05 was expressed as * in the graphs).

2. Results (1) Changes in the Spinal Cord

Effects of the single administration of reserpine on the amounts of dopamine, norepinephrine, serotonin, DOPAC, MHPG and 5-HIAA in the spinal cord are respectively shown in FIG. 7A, FIG. 7B, FIG. 7C, FIG. 7D, FIG. 7E and FIG. 7F. After 2, 4, 8 and 24 hours and 2, 3, 5, 7, 10, 14 and 21 days of the administration, reserpine significantly reduced each of the amounts of dopamine, norepinephrine and serotonin (two-way analysis of variance and the Bonferroni method). On the other hand, reserpine significantly increased the amount of DOPAC after 2, 4, 8 and 24 hours of its administration, and the amount of 5-HIAA after 4, 8, 24 hours and 2 days, but did not significantly change in both cases after 2 days or in and after 3 days after the administration (two-way analysis of variance and the Bonferroni method). In addition, reserpine significantly reduced the amount of MHPG after 4 hours and 7 days of the administration (two-way analysis of variance and the Bonferroni method). That is, in the spinal cord, amounts of dopamine, norepinephrine, serotonin and MHPG were reduced by the single subcutaneous administration of reserpine during both of the acute phase (within 24 hours after administration) and chronic phase (in and after 2 days of administration). On the other hand, amounts of DOPAC and 5-HIAA increased only during the acute phase (only DOPAC was increased after 2 days of administration), so that it was revealed that they show different changes during the acute phase and chronic phase.

(2) Changes in the Thalamus

Effects of the single administration of reserpine on the amounts of dopamine, norepinephrine, serotonin, DOPAC, MHPG and 5-HIAA in the thalamus are respectively shown in FIG. 8A, FIG. 8B, FIG. 8C, FIG. 8D, FIG. 8E and FIG. 8F. After 2, 4, 8 and 24 hours and 2, 3, 5, 7, 10, 14 and 21 days of the administration, reserpine significantly reduced each of the amounts of dopamine and norepinephrine and significantly reduced the amount of serotonin after 8 and 24 hours and 3, 5, 7 and 10 days of the administration (two-way analysis of variance and the Bonferroni method). On the other hand, reserpine significantly increased the amount of 5-HIAA after 2, 4, 8 and 24 hours of its administration, but there was no significant difference in and after 2 days of the administration (two-way analysis of variance and the Bonferroni method). In addition, reserpine did not significantly change the amounts of DOPAC and MHPG (two-way analysis of variance and the Bonferroni method). That is, in the thalamus, amounts of dopamine, norepinephrine and serotonin were reduced by the single subcutaneous administration of reserpine during both of the acute phase (within 24 hours after administration) and chronic phase (in and after 2 days of administration). On the other hand, the amount of 5-HIAA increased only during the acute phase, so that it was revealed that it shows different changes during the acute phase and chronic phase.

(3) Changes in the Prefrontal Cortex

Effects of the single administration of reserpine on the amounts of dopamine, norepinephrine, serotonin, DOPAC, MHPG and 5-HIAA in the prefrontal cortex are respectively shown in FIG. 9A, FIG. 9B, FIG. 9C, FIG. 9D, FIG. 9E and FIG. 9F. Reserpine significantly reduced the amount of dopamine after 2, 4, 8 and 24 hours and 2, 3, 5, 7, 10 and 14 days of the administration, the amount of norepinephrine after 2, 4, 8 and 24 hours and 2, 3, 5, 7, 10, 14 and 21 days of the administration and the amount of serotonin after 2, 4, 8 and 24 hours and 2, 3, 5, 7 and 10 days of the administration, respectively (two-way analysis of variance and the Bonferroni method). Also, reserpine significantly reduced the amount of MHPG after 4 hours and 7 days of the administration and the amount of 5-HIAA after 8 hours and 2, 3, 5, 7, 10, 14 and 21 days of the administration (two-way analysis of variance and the Bonferroni method). On the other hand, reserpine significantly reduced the amount of DOPAC after 2, 3, 5, 7, 10 and 14 days of the administration, but did not significantly change it within 24 hours after the administration (two-way analysis of variance and the Bonferroni method). That is, in the prefrontal cortex, amounts of dopamine, norepinephrine, serotonin, MHPG and 5-HIAA were reduced by the single subcutaneous administration of reserpine during both of the acute phase (within 24 hours after administration) and chronic phase (in and after 2 days of administration). On the other hand, amount of DOPAC was reduced only during the chronic phase, so that it was revealed that it shows different changes during the acute phase and chronic phase.

A summary of the changes in the biogenic amine levels and the levels of respective metabolites during the acute phase (within 24 hours after administration) by the single administration treatment of reserpine, and a summary of the changes in the biogenic amine levels and the levels of respective metabolites during the chronic phase (in and after 2 days of administration) by the single administration treatment of reserpine is shown in the following Table 1 and Table 2, respectively.

TABLE 1

|  | Dopamine | Dopamine metabolite DOPAC | Norepinephrine | Norepinephrine metabolite MHPG | Serotonin | Serotonin metabolite 5-HIAA |
|---|---|---|---|---|---|---|
| Spinal cord | ↓ | ⇑ | ↓ | ↓ | ↓ | ⇑ |
| Thalamus | ↓ | — | ↓ | — | ↓ | ⇑ |
| Prefrontal cortex | ↓ | — | ↓ | ↓ | ↓ | ↓ |

Downward arrow or upward arrow: Indicates that the object is significantly decreased, or significantly increased, in the reserpine-treated rat in comparison with the vehicle-treated rat at the time of measurement during acute phase (within 24 hours after administration) after the reserpine treatment.
—: Indicates that there is no statistical difference between the reserpine-treated rat and the vehicle-treated rat at the time of measurement during the acute phase after the reserpine treatment.
Note):
At the time of measurement during the acute phase after the reserpine treatment, the sensitivity for tactile (filament) stimulation and heat stimulation is accelerated, but the sensitivity for muscle pressure stimulation is decreased and the sensitivity for cold stimulation is not changed.

TABLE 2

|  | Dopamine | Dopamine metabolite DOPAC | Norepinephrine | Norepinephrine metabolite MHPG | Serotonin | Serotonin metabolite 5-HIAA |
|---|---|---|---|---|---|---|
| Spinal cord | ↓ | — | ↓ | ↓ | ↓ | — (Other than after 2 days) |
| Thalamus | ↓ | — | ↓ | — | ↓ | — |
| Prefrontal cortex | ↓ | ↓ | ↓ | ↓ | ↓ | ↓ |

Downward arrow or upward arrow: Indicates that the object is significantly decreased, or significantly increased, in the reserpine-treated rat in comparison with the vehicle-treated rat at the time of measurement during chronic phase (2 days or longer after administration) after the reserpine treatment.
—: Indicates that there is no statistical difference between the reserpine-treated rat and the vehicle-treated rat at the time of measurement during the chronic phase after the reserpine treatment.
Note):
At the time of measurement during the chronic phase after the reserpine treatment, all of the sensitivities for muscle pressure stimulation, tactile (filament) stimulation, cold stimulation and heat stimulation are accelerated.

Based on the results of Example 6, it was revealed that levels of the biogenic amine metabolites in the animals which received the reserpine treatment differ between the acute phase (within 24 hours after administration) and the chronic phase (2 days or longer after administration), depending on the species of the amine or the regions in the brain. Since it has been suggested that increase of the levels of biogenic amine metabolites means activation of biogenic amine signals (Roth et al., 1976), it is considered that the changes in the levels of biogenic amine metabolites are influencing upon the pain sensation threshold values. That is, it was shown that the difference in the pain sensation threshold values during chronic phase and acute phase described in Example 5 is due to the difference in activation conditions of the biogenic amine signals suggested by the levels of biogenic amine metabolites.

INDUSTRIAL APPLICABILITY

The disease animal model of the present invention which expresses both of chronic pain symptoms (chronic muscle pain and chronic tactile allodynia) and depressive symptom is extremely useful as a model that reflects disease states of chronic pains, particularly fibromyalgia, and substances as candidates of therapeutic agents for chronic pains, particularly fibromyalgia, can be efficiently evaluated by a screening method that uses this disease animal model.

The invention claimed is:

1. A method for screening for a therapeutic agent of a chronic pain, comprising administering a test substance to a disease animal model and measuring a muscle-pressure-pain threshold value and/or a skin-pain-sensation threshold value, wherein the disease animal model comprises inducing chronic pain, in a mammal without chronic pain, by applying to the mammal a treatment for reducing the biogenic amine level,
    wherein the treatment for reducing the biogenic amine level is repeated administration of an agent for reducing the biogenic amine level once a day until chronic pain is achieved in the mammal.

2. The method of claim 1, wherein the chronic pain is chronic muscle pain or chronic tactile allodynia.

3. The method of claim 2, wherein the chronic pain is further accompanied by a depressive symptom.

4. The method of claim 1, wherein the agent for reducing the biogenic amine level is reserpine.

5. The method of claim 1, wherein the mammal is a rodent.

6. The method of claim 1, wherein the rodent is a rat.

7. The method of claim 1, wherein the chronic pain is fibromyalgia.

* * * * *